United States Patent
Lassen (10) Patent No.: US 11,608,317 B2
(45) Date of Patent: Mar. 21, 2023

(54) TWO-STEP SYNTHESIS OF PYRROLE COMPOUNDS FROM FURAN COMPOUNDS

(71) Applicant: Chevron Phillips Chemical Company LP, The Woodlands, TX (US)

(72) Inventor: Kenneth M. Lassen, Bartlesville, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 101 days.

(21) Appl. No.: 17/202,481

(22) Filed: Mar. 16, 2021

(65) Prior Publication Data

US 2022/0298109 A1    Sep. 22, 2022

(51) Int. Cl.
| | | |
|---|---|---|
| *C07C 207/00* | (2006.01) | |
| *C07C 45/59* | (2006.01) | |
| *C07D 207/323* | (2006.01) | |
| *B01J 31/10* | (2006.01) | |
| *C07C 49/12* | (2006.01) | |

(52) U.S. Cl.
CPC .......... *C07D 207/323* (2013.01); *B01J 31/10* (2013.01); *C07C 45/59* (2013.01); *C07C 49/12* (2013.01)

(58) Field of Classification Search
CPC .................. C07C 207/223; C07C 45/59
See application file for complete search history.

(56) References Cited

U.S. PATENT DOCUMENTS

| | | | |
|---|---|---|---|
| 8,148,545 B2 | 4/2012 | Yang et al. | |
| 8,362,278 B2 | 1/2013 | Kreischer et al. | |
| 8,729,277 B2 | 5/2014 | Yang et al. | |
| 10,207,974 B1 | 2/2019 | Lassen et al. | |
| 2017/0073292 A1* | 3/2017 | De Campo | B01J 35/02 |

FOREIGN PATENT DOCUMENTS

| | | |
|---|---|---|
| CN | 101423467 A | 5/2009 |
| CN | 105348056 A | 2/2016 |
| CN | 105439836 A | 3/2016 |

OTHER PUBLICATIONS

Classical Organic Reactions in Pure Superheated Water, J. Org. Chem. 1994, 59, 3098-3101, Barbara Kuhlmann, et. al.
Functional Group Dependence of the acid Catalyzed Ring Opening of Biomass Furan Rings: An Experimental and Theoretical Study, Waidmann et. al., Catal. Sci. Technol., 2013, 3, pp. 106-115.
Intermediates in the Paal-Knorr Synthesis of Pyrroles, J. Org. Chem. 1991,56,6924-6931, Venkataraman Amarnath, et. al.
On the Bronsted Acid-Catalyzed Homogenous Hydrolysis Hydrolysis of Furans, Nikbin et. al., ChemSusChem, 2013, 6, pp. 2066-2068.
Organic Syntheses, Coll. vol. 2, p. 219 (1943), vol. 16 p. 25 (1936)—Young, et. al.—2,5-DimethylPyrrole.
Synthesis of 2,5-Hexanedione from Biomass Resources Using a Highly Efficient Biphasic System, Li et. al., ChemistrySelect, 2016, 6, pp. 1252-1255.

* cited by examiner

*Primary Examiner* — Sikarl A Witherspoon
(74) *Attorney, Agent, or Firm* — Merchant & Gould P.C.

(57) ABSTRACT

Pyrrole compounds are produced by contacting a furan compound, a solid acid catalyst, and water to form a reaction mixture containing a γ-dicarbonyl compound, and then contacting the γ-dicarbonyl compound with ammonia or an ammonium salt to form a reaction product mixture containing the pyrrole compound. A representative pyrrole compound that can be synthesized using these processes is 2,5-dimethylpyrrole.

21 Claims, 3 Drawing Sheets

TWO-STEP SYNTHESIS OF PYRROLE COMPOUNDS FROM FURAN COMPOUNDS

FIELD OF THE INVENTION

The present disclosure concerns processes for producing pyrrole compounds. More particularly, the present disclosure relates to contacting a furan compound, a solid acid catalyst, and water to form a γ-dicarbonyl compound, and then converting the γ-dicarbonyl compound to an analogous pyrrole compound.

BACKGROUND OF THE INVENTION

Pyrrole compounds, such as 2,5-dimethylpyrrole, can be used as components in oligomerization catalyst systems for producing α-olefins, such as 1-hexene or 1-octene, from ethylene. However, the synthesis schemes to produce pyrrole compounds and their γ-dicarbonyl precursors often suffer from one or more of low yield, large by-product formation, and difficult isolation and purification of the desired γ-dicarbonyl precursor compounds. Accordingly, the present invention is generally directed to a synthesis scheme to produce pyrrole compounds that overcomes these noted deficiencies.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes for producing a pyrrole compound are disclosed herein. These processes can comprise a) contacting a furan compound, a solid acid catalyst, and water to form a reaction mixture comprising a γ-dicarbonyl compound, and b) contacting the γ-dicarbonyl compound with ammonia, an ammonium salt, or a combination thereof, to form a reaction product mixture comprising the pyrrole compound.

While not limited thereto, in the processes described herein, the furan compound (F1), the γ-dicarbonyl compound (D1), and the pyrrole compound (P1) can have the following formulas:

In these formulas, R, $R^1$, $R^2$, and $R^3$ independently can be a hydrogen atom, a $C_1$-$C_{30}$ organyl group, or a $C_3$-$C_{60}$ silyl group. In a particular aspect, R and $R^1$ can be methyl groups, and $R^2$ and $R^3$ can be hydrogen atoms.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description and examples.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or statements, a combination of different features can be envisioned. For each and every aspect, and/or statement, and/or feature disclosed herein, all combinations that do not detrimentally affect the systems, compositions, processes, and/or methods described herein are contemplated with or without explicit description of the particular combination. Additionally, unless explicitly recited otherwise, any aspect, and/or statement, and/or feature disclosed herein can be combined to describe conceived processes and systems consistent with the present disclosure.

The terms "a," "an," and "the" are intended to include plural alternatives, e.g., at least one, unless otherwise specified. For instance, the disclosure of "a furan compound" or "a solid acid catalyst" is meant to encompass one, or mixtures or combinations of more than one, furan compound or solid acid catalyst, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. An "organyl group," "organylene group," or "organic group" can be aliphatic, (inclusive of being cyclic or acyclic, or linear or branched), or can be aromatic.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "γ-dicarbonyl compound" refers to a compound having two ketone groups, two aldehyde groups, or an aldehyde group and a ketone group, separated by two contiguous carbon atoms. While the γ-dicarbonyl compound must contain at least the two groups in the designated relationship, these compounds can contain additional aldehyde and/or ketone groups, which may or may not have the designated relationship. Additionally, unless otherwise specified, the γ-dicarbonyl compound can contain other heteroatoms and/or functional groups (e.g., ester or amide groups).

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Within this disclosure, the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4-position and hydrogens located at the 2, 3, 5, and 6 positions. References to compounds or groups having substitutions at positions in addition to the indicated position can be referenced using comprising or some other alternative language. For example, a reference to a phenyl group comprising a substituent at the 4-position refers to a phenyl group having a non-hydrogen substituent at the 4-position and hydrogen or any non-hydrogen substituent at the 2, 3, 5, and 6 positions.

The term "contacting" is used herein to describe systems, compositions, processes, and methods in which the components are contacted or combined together in any order, in any manner, and for any length of time, unless otherwise specified. For example, the components can be combined by blending or mixing, using any suitable technique. Herein, "contacting" two or more components can result in a reaction product mixture or a reaction mixture.

In this disclosure, while compositions and processes are described in terms of "comprising" various components or steps, the compositions and processes also can "consist essentially of" or "consist of" the various components or steps, unless stated otherwise.

All disclosed product yields are based on the limiting reactant in the respective reaction, unless explicitly stated otherwise. For example, the limiting reactant in a catalytic process that results in a γ-dicarbonyl compound can be a furan compound and, therefore, the yield of the γ-dicarbonyl compound would be based on the initial quantity of the furan compound. In non-catalytic reactions or conversions, the limiting reactant is the reactant which is not present in sufficient number of moles to react with the other reactant(s) according to the reaction stoichiometry.

Although any methods and materials similar or equivalent to those described herein can be used in the practice or testing of the processes and reaction systems, the typical methods and materials are herein described.

All publications and patents mentioned herein are incorporated herein by reference for the purpose of describing and disclosing, for example, the constructs and methodologies that are described in the publications, which might be used in connection with the present disclosure.

DETAILED DESCRIPTION OF THE INVENTION

Disclosed herein are processes for producing pyrrole compounds by contacting a furan compound, a solid acid catalyst, and water to form a reaction mixture comprising a γ-dicarbonyl compound, and contacting the γ-dicarbonyl compound with ammonia, an ammonium salt, or a combination thereof, to form a reaction product mixture comprising the pyrrole compound.

Generally, the features of the processes for producing a pyrrole compound (e.g., the furan compound, the dicarbonyl compound, the pyrrole compound, the solid acid catalyst, the ammonium salt, the conditions under which the dicarbonyl compound is formed, and the conditions under which the pyrrole compound is formed, among others) are independently described herein and these features can be utilized without limitation and in any combination to further describe the disclosed processes to produce a pyrrole compound. Moreover, additional process steps can be performed before, during, and/or after any steps of the disclosed processes, and can be utilized without limitation and in any combination to further describe the pyrrole synthesis processes, unless stated otherwise.

Advantageously, the processes disclosed herein provide a surprisingly high conversion of the furan compound and yield to the γ-dicarbonyl compound, with minimal by-products. Further, the dicarbonyl compound can be easily isolated and purified prior to conversion to the desired pyrrole compound.

Synthesizing Gamma Dicarbonyl Compounds

In step a) of the process for producing a pyrrole compound, a furan compound, a solid acid catalyst, and water can be contacted to form a reaction mixture comprising a γ-dicarbonyl compound. While not limited thereto, the furan compound (F1) and the γ-dicarbonyl compound (D1) in step a) can have the following formulas:

In these formulas, R, $R^1$, $R^2$, and $R^3$ independently can be a hydrogen atom, a $C_1$-$C_{30}$ organyl group, or a $C_3$-$C_{60}$ silyl group. It is contemplated that any of R, $R^1$, $R^2$, and $R^3$ can be the same or different.

In an aspect, R, $R^1$, $R^2$, and $R^3$ independently can be hydrogen, a $C_1$ to $C_{18}$ organyl group (such as a $C_1$ to $C_{18}$ hydrocarbyl group), or a $C_3$-$C_{48}$ silyl group. In another aspect, R, $R^1$, $R^2$, and $R^3$ independently can be hydrogen, a $C_1$ to $C_{12}$ organyl group (such as a $C_1$ to $C_{12}$ hydrocarbyl group), or a $C_3$-$C_{36}$ silyl group. In yet another aspect, R, $R^1$, $R^2$, and $R^3$ independently can be hydrogen, a $C_1$ to $C_8$ organyl group (such as a $C_1$ to $C_8$ hydrocarbyl group), or a $C_3$-$C_{24}$ silyl group. Thus, R, $R^1$, $R^2$, and $R^3$ independently can be hydrogen or a $C_1$ to $C_{18}$ hydrocarbyl group (or a $C_1$ to $C_{12}$ or a $C_1$ to $C_8$ hydrocarbyl group).

In an aspect, any of R, $R^1$, $R^2$, and/or $R^3$ independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the alkyl group can be a $C_1$ to $C_{20}$, a $C_1$ to $C_{10}$, or a $C_1$ to $C_5$ alkyl group. In any aspect disclosed herein, the substituted alkyl group can be a $C_1$ to $C_{20}$, a $C_1$ to $C_{10}$, or a $C_1$ to $C_5$ substituted alkyl group. In any aspect disclosed herein, the cycloalkyl group can be a $C_4$ to $C_{20}$, a $C_4$ to $C_{15}$, or a $C_4$ to $C_{10}$ cycloalkyl group. In any aspect disclosed herein, the substituted cycloalkyl group can be a $C_4$ to $C_{20}$, a $C_4$ to $C_{15}$, or a $C_4$ to $C_{10}$ substituted cycloalkyl group. In any aspect disclosed herein, the aryl group can be a $C_6$ to $C_{20}$, a $C_6$ to $C_{15}$, or a $C_6$ to $C_{10}$ aryl group. In any aspect disclosed herein, the substituted aryl group can be a $C_6$ to $C_{20}$, a $C_6$ to $C_{15}$, or a $C_6$ to $C_{10}$ substituted aryl group. In any aspect disclosed herein, the aralkyl group can be a $C_7$ to $C_{20}$, a $C_7$ to $C_{15}$, or a $C_7$ to $C_{10}$ aralkyl group. In any aspect disclosed herein, the substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or a substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted R, $R^1$, $R^2$, and/or $R^3$ group.

In an aspect, any of R, $R^1$, $R^2$, and/or $R^3$ independently can be a methyl group, an ethyl group, a propyl group, a butyl group, a pentyl group, a hexyl group, a heptyl group, or an octyl group; or alternatively, a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as any of R, $R^1$, $R^2$, and/or $R^3$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as any of R, $R^1$, $R^2$, and/or $R^3$.

In an aspect, any of R, $R^1$, $R^2$, and/or $R^3$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group which can be utilized as any of R, $R^1$, $R^2$, and/or $R^3$ can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as any of R, $R^1$, $R^2$, and/or $R^3$ can be the same or different; alternatively, all the substituents of a multi-substituted cycloalkyl group can be the same; or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as any of R, $R^1$, $R^2$, and/or $R^3$.

In a non-limiting aspect, any of R, $R^1$, $R^2$, and/or $R^3$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general or specific), and/or dialkylcyclopentyl groups (general and specific) which can be utilized as any of R, $R^1$, $R^2$, and/or $R^3$. Generally, the alkyl substituents of a dialkylcyclohexyl group or a dialkylcyclopentyl group can be the same; or alternatively, the alkyl substituents of a dialkylcyclohexyl group or a dialkylcyclopentyl group can be different. In some non-limiting aspects, any of R, $R^1$, $R^2$, and/or $R^3$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, any of R, $R^1$, $R^2$, and/or $R^3$ independently can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, any of R, $R^1$, $R^2$, and/or $R^3$ independently can be a phenyl group or a substituted phenyl group; alternatively, a phenyl group; or alternatively, a substituted phenyl group. In an aspect, the substituted phenyl group which can be utilized as any of R, $R^1$, $R^2$, and/or $R^3$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as any of R, $R^1$, $R^2$, and/or $R^3$ can be the same or different; alternatively, all the substituents of a multi-substituted phenyl group can be the same; or alternatively, all the substituents of a multi-substituted phenyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as any of R, $R^1$, $R^2$, and/or $R^3$.

In a non-limiting aspect, any of R, $R^1$, $R^2$, and/or $R^3$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as any of R, $R^1$, $R^2$, and/or $R^3$. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting aspects, any of R, $R^1$, $R^2$, and/or $R^3$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an aspect, any of R, $R^1$, $R^2$, and/or $R^3$ independently can be a benzyl group or a substituted benzyl group; alternatively, a benzyl group; or alternatively, a substituted benzyl group.

Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as any of R, $R^1$, $R^2$, and/or $R^3$.

In an aspect, any of R, $R^1$, $R^2$, and/or $R^3$ independently can be an acyl group or a substituted acyl group; an acyl group; or alternatively, a substituted acyl group. In an aspect, the acyl group can be a $C_1$ to $C_{20}$, a $C_1$ to $C_{15}$, a $C_1$ to $C_{10}$, or a $C_1$ to $C_5$ acyl group. In an aspect, the substituted acyl group can be a $C_1$ to $C_{20}$, a $C_1$ to $C_{15}$, a $C_1$ to $C_{10}$, or a $C_1$ to $C_5$ substituted acyl group. In some aspects, any of R, $R^1$, $R^2$, and/or $R^3$ independently can be an alkanoyl group, a substituted alkanoyl group, a benzoyl group, or a substituted benzoyl group; alternatively, an alkanoyl group or a substituted alkanoyl group; alternatively, a benzoyl group or a substituted benzoyl group; alternatively, an alkanoyl group; alternatively, a substituted alkanoyl group; alternatively, a benzoyl group; or alternatively, a substituted benzoyl group. In any aspect disclosed herein, the alkanoyl group can be a $C_1$ to $C_2$, a $C_1$ to $C_{10}$, or a $C_1$ to $C_5$ alkanoyl group. In any aspect disclosed herein, the substituted alkanoyl group can be a $C_1$ to $C_{20}$, a $C_1$ to $C_{10}$, or a $C_1$ to $C_5$ substituted alkanoyl group. In any aspect disclosed herein, the benzoyl group can be a $C_7$ to $C_{20}$, a $C_7$ to $C_{15}$, or a $C_7$ to $C_{10}$ benzoyl group. In any aspect disclosed herein, the substituted benzoyl group can be a $C_7$ to $C_{20}$, a $C_1$ to $C_{15}$, or a $C_1$ to $C_{10}$ substituted benzoyl group. Each substituent of a substituted alkanoyl group (general or specific) and/or substituted benzoyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe substituted alkanoyl groups and/or substituted benzoyl group which can be utilized as any of R, $R^1$, $R^2$, and/or $R^3$.

Various aspects described herein refer to non-hydrogen substituents such as halogen (or halo, halide), hydrocarbyl, hydrocarboxy, alkyl, and/or alkoxy substituents. In an aspect, each non-hydrogen substituent of any aspect calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Each hydrocarbyl substituent independently can be a $C_1$ to $C_{10}$ hydrocarbyl group; or alternatively, a $C_1$ to $C_5$ hydrocarbyl group. Each hydrocarboxy substituent independently can be a $C_1$ to $C_{10}$ hydrocarboxy group; or alternatively, a $C_1$ to $C_5$ hydrocarboxy group. Each halide substituent independently can be a fluoride, chloride, bromide, or iodide; alternatively, a fluoride or chloride; alternatively, a fluoride; alternatively, a chloride; alternatively, a bromide; or alternatively, an iodide.

In an aspect, any hydrocarbyl substituent independently can be an alkyl group, an aryl group, or an aralkyl group; alternatively, an alkyl group; alternatively, an aryl group; or alternatively, an aralkyl group. In an aspect, any alkyl substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an aspect, any aryl substituent independently can be phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an aspect, any aralkyl substituent independently can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an aspect, any hydrocarboxy substituent independently can be an alkoxy group, an aryloxy group, or an aralkoxy group; alternatively, an alkoxy group; alternatively, an aryloxy group; or alternatively, an aralkoxy group. In an aspect, any alkoxy substituent independently can be a methoxy group, an ethoxy group, a n-propoxy group, an isopropoxy group, a n-butoxy group, a sec-butoxy group, an isobutoxy group, a tert-butoxy group, a n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an aspect, any aryloxy substituent independently can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an aspect, any aralkoxy substituent independently can be benzoxy group.

In an aspect, any of R, $R^1$, $R^2$, and/or $R^3$ independently can be a $C_3$-$C_{60}$ silyl group; alternatively, a $C_3$-$C_{48}$ silyl group; alternatively, a $C_3$-$C_{36}$ silyl group; alternatively, a $C_3$-$C_{24}$ silyl group; or alternatively, a $C_3$ to $C_{15}$ silyl group. In some aspects, the silyl group(s) which can be any of R, $R^1$, $R^2$, and/or $R^3$ can have formula (Si1):

(Si1)

Generally, $R^{1s}$, $R^{2s}$, and $R^{3s}$, of the silyl group having formula Si1 independently can be an organyl group or a hydrocarbyl group; alternatively, an organyl group; or alternatively, a hydrocarbyl group. The organyl groups and/or the hydrocarbyl groups which can be utilized as $R^{1s}$, $R^{2s}$, and $R^{3s}$ of the silyl group having formula Si1 can have the numbers of carbons as those of the organyl groups and hydrocarbyl groups disclosed herein as non-hydrogen furan and dicarbonyl substituents. For instance, $R^{1s}$, $R^{2s}$, and $R^{3s}$ independently can be a $C_1$ to $C_{15}$ hydrocarbyl group. In an aspect, $R^{1s}$, $R^{2s}$, and $R^{3s}$ of the silyl group having formula Si1 independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group. Alkyl groups, substituted alkyl groups, cycloalkyl groups, substituted cycloalkyl groups, aryl groups, substituted aryl groups, aralkyl groups, and substituted aralkyl groups have been independently described herein as potential non-hydrogen furan and dicarbonyl substituents and can be utilized, without limitation, as $R^{1s}$, $R^{2s}$, and $R^{3s}$ of the silyl group having formula Si1.

In an aspect, any silyl groups which can be utilized as any of R, $R^1$, $R^2$, and/or $R^3$ independently can be a trihydrocarbylsilyl group. In some aspects, the silyl group can be a trialkylsilyl group (e.g., a trimethylsilyl group, a triethylsilyl group, a triisopropylsilyl group, or a tri-t-butylsilyl group), a triphenylsilyl group, or a tri(substituted phenyl)silyl group; alternatively, a trialkylsilyl group; alternatively, a triphenylsilyl group; or alternatively, a tri(substituted phenyl)silyl group. Hydrocarbyl groups, alkyl groups, and substituted phenyl groups have been independently described herein as potential non-hydrogen furan and dicarbonyl substituents and can be utilized, without limitation, as $R^{1s}$, $R^{2s}$, and $R^{3s}$ of the silyl group having formula Si1.

In some aspects herein, at least one of R, $R^1$, $R^2$, and $R^3$ is not a hydrogen atom. For instance, R and $R^1$ independently can be a $C_1$-$C_{18}$ hydrocarbyl group, and $R^2$ and $R^3$ can be a hydrogen atom. Suitable hydrocarbyl groups are disclosed herein, such that R and $R^1$ independently can be, for example, a methyl group, an ethyl group, a n-propyl group, an iso-propyl group, a n-butyl group, a t-butyl group, a phenyl group, a benzyl group, a tolyl group, or a xylyl group. In a particular aspect, R and $R^1$ can be a methyl group, and $R^2$ and $R^3$ can be hydrogen.

In an aspect, the furan compound utilized in the disclosed processes can comprise (or consist essentially of, or consist of) 2,5-dimethylfuran, 2,5-diethylfuran, 2-ethyl-5-methylfuran, 2-ethyl-5-n-propylfuran, 2,5-di-n-propylfuran, 2,5-diisopropylfuran, 2,5-di-n-butylfuran, 2,5-di-n-pentylfuran, 2,5-di-n-hexylfuran, 2,5-di-n-heptylfuran, 2,5-di-n-octylfuran, 2,3,5-triethylfuran, 2,3,5-tri-n-butylfuran, 2,3,5-tri-n-pentylfuran, 2,3,5-tri-n-hexylfuran, 2,3,5-tri-n-heptylfuran, 2,3,5-tri-n-octylfuran, 2,3,4,5-tetraethylfuran, 2,3,4,5-tetra-n-butylfuran, 2,3,4,5-tetra-n-hexylfuran, 2,5-dibenzylfuran, 2,4-dimethylfuran, 2-methyl-4-isopropylfuran, 2,4-dimethyl-3-ethylfuran, 2,4-diethylfuran, 2-ethyl-4-isopropylfuran, 2-methyl-4-sec-butylfuran, 2-ethyl-4-sec-butylfuran, 2-methyl-4-isobutylfuran, 2-ethyl-4-isobutylfuran, 2-methyl-4-t-butylfuran, 2-ethyl-4-t-butylfuran, 2-methyl-4-neopentylfuran, 2-ethyl-4-neopentylfuran, 3,4-dimethylfuran, 3,4-diethylfuran, 3,4-diisopropylfuran, 3,4-di-sec-butylfuran, 3,4-diisobutylfuran, 3,4-di-t-butylfuran, 3,4-di-neopentylfuran, and the like, as well as any combination thereof. In a particular aspect consistent with this invention, the furan compound utilized by the disclosed processes can comprise (or consist essentially of, or consist of) 2,5-dimethylfuran.

Surprisingly, step a) to produce the γ-dicarbonyl compound herein can be particularly effective when the furan compound and the solid acid catalyst are contacted with water. While not wishing to be bound by theory, the improvements in reaction yield and conversion observed when water is used may be the result of water promoting the reaction of the furan compound and the solid acid catalyst, for instance, by stabilizing a transition state between the one or more reactants and a product or intermediate thereof. However, water may increase the conversion of the furan compound and yield to the γ-dicarbonyl compound by any other means.

Generally, the appropriate procedure for the contacting (or reacting) in step a) is not particularly limited. For instance, the furan compound, the solid acid catalyst, and water can be contacted in any order, method, or process that produces an acceptable yield of the γ-dicarbonyl compound. In an aspect, the furan compound can be mixed with water prior to contacting the solid acid catalyst.

Certain ratios of components during step a) can prove advantageous with respect to furan conversion and yield of the γ-dicarbonyl compound. For instance, step a) can be conducted at a minimum molar ratio of water to the furan compound of at least 0.25:1, 0.5:1, 1:1, or 1.5:1; additionally or alternatively, step a) can be conducted at a maximum molar ratio of water:furan compound of less than or equal to 50:1, 25:1, 10:1, 7.5:1, or 5:1. Generally, the water:furan compound molar ratio can be in a range from any minimum molar ratio disclosed herein to any maximum molar ratio disclosed herein. Accordingly, suitable non-limiting ranges for the water:furan compound molar ratio can include the following: from 0.25:1 to 50:1, from 1:1 to 50:1, from 0.5:1 to 25:1, from 0.5:1 to 10:1, from 1:1 to 10:1, from 1:1 to 7.5:1, or from 1.5:1 to 5:1. Other appropriate ranges for the molar ratio of water:furan compound in step a) are readily apparent from this disclosure.

Typically, step a) can be conducted at any pressure sufficient to maintain water in the liquid phase. For instance, step a) can be conducted at pressure of at least 5 psig (34 kPa), 10 psig (69 kPa), 25 psig (172 kPa), 40 psig (276 kPa), or 50 psig (345 kPa); additionally or alternatively, step a) can be conducted at a pressure of less than or equal to 200 psig (1.38 MPa), 175 psig (1.21 MPa), 150 psig (1.03 MPa), or 125 psig (0.86 MPa). Generally, the pressure in step a) can range from any minimum pressure disclosed herein to any maximum pressure disclosed herein.

Therefore, suitable non-limiting ranges for the pressure in step a) can include the following ranges: from 5 psig (34 kPa) to 200 psig (1.38 MPa), from 10 psig (69 kPa) to 200 psig (1.38 MPa), from 25 psig (172 kPa) to 175 psig (1.21 MPa), from 25 psig (172 kPa) to 150 psig (1.03 MPa), from 40 psig (276 kPa) to 150 psig (1.03 MPa), or from 50 psig (345 kPa) to 125 psig (0.86 MPa). Other appropriate pressure ranges for step a) and for the formation of the γ-dicarbonyl compound are readily apparent from this disclosure. These pressure ranges also are meant to encompass circumstances where step a) (or the formation of the γ-dicarbonyl compound) is performed at a series of different pressures, instead of at a single fixed pressure, falling within the respective pressure ranges.

In an aspect, step a) can be conducted at any temperature below the maximum operating temperature (or thermal stability temperature) of the solid acid catalyst. In another aspect, step a) can be conducted at any temperature below the melting temperature of the solid acid catalyst, or step a) can be conducted at any temperature below the softening point/temperature of the solid acid catalyst. For instance, and depending upon the particular solid acid catalyst, step a) can be conducted at a minimum temperature of 80° C., 90° C., 100° C., 110° C., or 120° C.; additionally or alternatively, at a maximum temperature 180° C., 170° C., 155° C., or 150° C. Generally, the temperature in step a) can range from any minimum temperature disclosed herein to any maximum temperature disclosed herein. Accordingly, suitable non-limiting ranges for the temperature in step a) and for the formation of the γ-dicarbonyl compound can include the following: from 80° C. to 180° C., from 80° C. to 155° C., from 90° C. to 170° C., from 90° C. to 155° C., from 100° C. to 170° C., from 100° C. to 155° C., from 110° C. to 170° C., from 110° C. to 150° C., from 120° C. to 180° C., from 120° C. to 175° C., or from 120° C. to 150° C. Other appropriate temperatures and temperature ranges are readily apparent from this disclosure. These temperature ranges also are meant to encompass circumstances where step a) (or the formation of the γ-dicarbonyl compound) is performed at a series of different temperatures, instead of at a single fixed temperature, falling within the respective temperature ranges.

In an aspect, step a) can be conducted in a stirred tank reactor. The time period for contacting the furan compound, the solid acid catalyst, and water (or for the formation of the γ-dicarbonyl compound) in the stirred tank reactor is not particularly limited, and can be conducted for any suitable period of time. Nonetheless, the minimum average residence time in the stirred tank reactor for step a) can be 5 min, 10 min, 15 min, 30 min, or 1 hr; additionally or alternatively, the maximum average residence time can be 10 hr, 8 hr, 7 hr, 5 hr, or 3 hr. Generally, the average residence time in the stirred tank reactor for step a) can be in a range from any minimum time disclosed herein to any maximum time disclosed herein. Accordingly, suitable non-limiting ranges for the average residence time can include the following: from 5 min to 10 hr, from 10 min to 8 hr, from 15 min to 7 hr, from 30 min to 5 hr, from 30 min to 3 hr, from 1 hr to 10 hr, from 1 hr to 7 hr, from 1 hr to 5 hr, or from 1 hr to 3 hr. Other appropriate ranges for the average residence time are readily apparent from this disclosure.

The weight ratio of the furan compound to the solid acid catalyst (furan:catalyst) in the stirred tank reactor is not particularly limited. In an aspect, step a) can be conducted at a minimum weight ratio of furan:catalyst of at least 5:1, 7.5:1, or 10:1; additionally or alternatively, step a) can be conducted at a maximum weight ratio of furan:catalyst of less than or equal to 50:1, 40:1, or 25:1. Generally, the furan:catalyst weight ratio can be in a range from any minimum weight ratio disclosed herein to any maximum weight ratio disclosed herein. Accordingly, suitable non-limiting ranges for the furan:catalyst weight ratio can include the following: from 5:1 to 50:1, from 5:1 to 25:1, from 7.5:1 to 40:1, from 7.5:1 to 25:1, from 10:1 to 50:1, from 10:1 to 40:1, or from 10:1 to 25:1. Other appropriate ranges for the weight ratio of furan:catalyst in step a) are readily apparent from this disclosure.

In an aspect, step a) can be conducted in a fixed bed reactor. In such aspects, the furan compound-catalyst contact time (or reaction time) can be expressed in terms of weight hourly space velocity (WHSV)—the ratio of the weight of the furan compound reactant which comes in contact with a given weight of the solid acid catalyst per unit time (units of g/g/hr). While not limited thereto, step a) can be conducted at a minimum WHSV value of 0.01, 0.05, 0.1, 0.15, or 0.2;

additionally or alternatively, step a) can be conducted at a maximum WHSV value of 10, 5, 4, 3, 2, or 1. Generally, the WHSV for step a) can be in a range from any minimum WHSV disclosed herein to any maximum WHSV disclosed herein. Accordingly, suitable non-limiting ranges for the WHSV can include the following: from 0.01 to 10, from 0.01 to 5, from 0.05 to 4, from 0.05 to 2, from 0.1 to 10, from 0.1 to 3, from 0.15 to 4, from 0.15 to 2, from 0.2 to 3, or from 0.2 to 1. Other appropriate WHSV ranges are readily apparent from this disclosure.

In a fixed bed reactor aspect, the conversion of the furan compound to the γ-dicarbonyl compound can be accomplished via multiple passes through the fixed bed reactor; or alternatively, in a single pass through the fixed bed reactor(s). In aspects where the conversion of the furan compound to the γ-dicarbonyl compound can be accomplished via multiple passes through the fixed bed reactor, the average single pass conversion of the furan compound (or the average single pass molar yield to the γ-dicarbonyl compound) can be at least 5 mol %, at least 10 mol %, at least 15 mol %, at least 20 mol %, or at least 25 mol %; additionally or alternatively, the average single pass conversion of the furan compound (or the average single pass molar yield to the γ-dicarbonyl compound) can be less than or equal to 75 mol %, less than or equal to 60 mol %, less than or equal to 50 mol %, less than or equal to 40 mol %, or less than or equal to 30 mol %. Generally, the average single pass conversion of the furan compound (or the average single pass molar yield to the γ-dicarbonyl compound) can be in a range from any minimum average single pass conversion of the furan compound (or minimum average single pass molar yield to the γ-dicarbonyl compound) disclosed herein to any maximum average single pass conversion of the furan compound (or maximum average single pass molar yield to the γ-dicarbonyl compound) disclosed herein. Accordingly, suitable non-limiting ranges for the average single pass conversion of the furan compound (or average single pass molar yield to the γ-dicarbonyl compound) can include the following: from 5 mol % to 75 mol %, from 10 mol % to 60 mol %, from 10 mol % to 50 mol %, from 15 mol % to 40 mol %, from 20 mol % to 40 mol %, or 10 mol % to 30 mol %. Other appropriate ranges for the average single pass conversion of the furan compound (or average single pass molar yield to the γ-dicarbonyl compound) are readily apparent from this disclosure. Generally, the molar yield is based on the moles of the furan compound.

Unexpectedly, step a), whether practiced in a stirred tank reactor or a fixed bed reactor, efficiently converts the furan compound and produces the γ-dicarbonyl compound in a higher yield than that observed in analogous reactions using different catalysts and/or not in the presence of water. The total conversion of the furan compound (or a total molar yield to the γ-dicarbonyl compound) in step a) can be at least 70 mol %, and more often, at least 80 mol %, at least 85 mol %, at least 90 mol %, at least 95 mol %, or at least 97 mol %. The total molar yield is based on the moles of the furan compound.

Unless otherwise indicated, the compositional aspects of dicarbonyl products (or reaction mixtures containing dicarbonyl products) are disclosed in mol %. Any disclosure herein of a compositional aspect in mol % also can be meant to encompass the same compositional aspect in area % (area percentage determined using a gas chromatograph, as described herein), because the disclosed processes and resultant products are often analyzed or evaluated in this manner. While conversion of the furan compound in area % or mol % can be utilized, these conversions using area % and mol % are not identical. As a representative example, a disclosure that the γ-dicarbonyl compound can be produced in a yield of at least 90 mol % is meant also to alternatively disclose that the γ-dicarbonyl compound can be produced in a yield of at least 90 area %.

The processes to produce the pyrrole compound disclosed herein, after step a), typically result in a reaction mixture containing the desired γ-dicarbonyl compound, residual furan reactant, solid catalyst, water, and by-products. In many instances, it can be desirable to isolate or separate at least a portion (and in some cases, all) of the γ-dicarbonyl compound from the reaction mixture after step a). This can be accomplished using any suitable technique, which can include but is not limited to, extraction, filtration, evaporation, or distillation, as well as combinations of two or more of these techniques.

Additionally or alternatively, the processes disclosed herein can further comprise a step of separating at least a portion (and in some cases, all) of the solid acid catalyst from the reaction mixture after step a) using any suitable technique or any technique disclosed herein, e.g., extraction, filtration, evaporation, distillation, or any combination thereof, prior to step b). For instance, the solid acid catalyst can be separated from the reaction mixture and the remaining reaction mixture then can be used in step b), or alternatively, isolated γ-dicarbonyl compound from the reaction mixture can be used in step b).

Synthesizing Pyrrole Compounds

In step b), the γ-dicarbonyl compound (in the reaction mixture from step a) or partially or completely separated therefrom) can be contacted with ammonia, an ammonium salt, or a combination thereof, to form a reaction product mixture comprising the pyrrole compound. While not limited thereto, the pyrrole compound can have the following formula:

The pyrrole compound is formed from the furan compound (e.g., furan compound (F1) through the γ-dicarbonyl compound (e.g., γ-dicarbonyl compound (D1)). Consequently, R, $R^1$, $R^2$, and $R^3$ in formula (P1) are the same as those described herein for furan compound (F1) and γ-dicarbonyl compound (D1). Hence, R, $R^1$, $R^2$, and $R^3$ independently can be a hydrogen atom, any $C_1$-$C_{30}$ organyl group disclosed herein, or any $C_3$-$C_{60}$ silyl group disclosed herein. For example, R, $R^1$, $R^2$, and $R^3$ independently can be a hydrogen atom or a $C_1$-$C_{18}$ hydrocarbyl group; alternatively, R and $R^1$ independently can a $C_1$-$C_{18}$ hydrocarbyl group, and $R^2$ and $R^3$ can be a hydrogen atom; or alternatively, R and $R^1$ can be a methyl group, and $R^2$ and $R^3$ can be a hydrogen atom.

In an aspect, the pyrrole compound prepared by the disclosed processes can comprise (or consist essentially of, or consist of) 2,5-dimethylpyrrole, 2,5-diethylpyrrrole, 2-ethyl-5-methylpyrrole, 2-ethyl-5-n-propylpyrrole, 2,5-di-n-propylpyrrole, 2,5-diisopropylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,3,5-triethylpyrrrole, 2,3,5-tri-n-butylpyrrole, 2,3,5-tri-n-pentylpyrrole, 2,3,5-trin-hexylpyrrole, 2,3,5-tri-n-heptylpyrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-dibenzylpyrrole, 2,4-dimethylpyrrole, 2-methyl-4-isopropylpyrrole, 2,4-dimethyl-3-ethylpyrrole, 2,4-diethylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-dimethylpyrrole, 3,4-diethylpyrrole, 3,4-diisopropylpyrrole, 3,4-di-sec-butylpyrrole, 3,4-diisobutylpyrrole, 3,4-di-t-butylpyrrole, 3,4-di-neopentylpyrrole, and the like, as well as any combination thereof. In a particular aspect consistent with this invention, the pyrrole compound prepared by the disclosed processes can comprise (or consist essentially of, or consist of) 2,5-dimethylpyrrole.

The γ-dicarbonyl compound (used as obtained from step a) or partially or completely separated therefrom) can be contacted with ammonia and/or an ammonium salt to form a reaction product mixture comprising the desired pyrrole compound in step b). In one aspect, step b) can comprise contacting the γ-dicarbonyl compound with ammonia. In another aspect, step b) can comprise contacting the γ-dicarbonyl compound with an ammonium salt. Non-limiting examples of suitable ammonium salts include ammonium hydroxide (e.g., liquid ammonium hydroxide as a solution of ammonia in water), ammonium acetate, ammonium carbonate, ammonium bicarbonate, ammonium chloride, ammonium nitrate, ammonium phosphate, ammonium sulfate, and the like, as well as combinations thereof. Hence, step b) can comprise contacting the γ-dicarbonyl compound with ammonium hydroxide; alternatively, ammonium acetate; alternatively, ammonium carbonate; alternatively, ammonium bicarbonate; alternatively, ammonium chloride; alternatively, ammonium nitrate; alternatively, ammonium phosphate; or alternatively, ammonium sulfate.

Step b) can conducted at any suitable temperature. While not limited thereto, step b) can be conducted at a minimum temperature of 50° C., 60° C., 70° C., 80° C., or 90° C.; additionally or alternatively, at a maximum temperature 170° C., 160° C., 150° C., 140° C., or 130° C. Generally, the temperature in step b) can range from any minimum temperature disclosed herein to any maximum temperature disclosed herein. Accordingly, suitable non-limiting ranges for the temperature in step b) and for the formation of the pyrrole compound can include the following: from 50° C. to 170° C., from 60° C. to 160° C., from 70° C. to 150° C., from 80° C. to 160° C., from 80° C. to 130° C., from 90° C. to 170° C., or from 90° C. to 140° C. Other appropriate temperatures and temperature ranges are readily apparent from this disclosure. These temperature ranges also are meant to encompass circumstances where step b) (or the formation of the pyrrole compound) is performed at a series of different temperatures, instead of at a single fixed temperature, falling within the respective temperature ranges.

The duration of step b) also is not particularly limited. Nonetheless, the minimum contact time (or reaction time) for step b) can be 15 min, 30 min, 1 hr, or 2 hr; additionally or alternatively, the maximum contact time (or reaction time) can be 10 hr, 8 hr, 6 hr, 5 hr, or 4 hr. Generally, the contact time (or reaction time) for step b) can be in a range from any minimum time disclosed herein to any maximum time disclosed herein. Accordingly, suitable non-limiting ranges for the contact time (or reaction time) time can include the following: from 15 min to 10 hr, from 30 min to 8 hr, from 30 min to 4 hr, from 1 hr to 6 hr, from 1 hr to 4 hr, from 2 hr to 10 hr, from 2 hr to 6 hr, or from 2 hr to 5 hr. Other appropriate ranges for the duration of step b) are readily apparent from this disclosure.

The reaction product mixture in step b) comprises the desired pyrrole compound. However, often the reaction product mixture can have two phases and comprises an organic phase and an aqueous phase. It can be beneficial to remove the aqueous phase from the reaction product mixture, thus the disclosed processes can further comprise a step of separating at least a portion (and in some cases, all) of the water from the reaction product mixture (e.g., using a phase cut) after step b).

Additionally or alternatively, the processes to produce the pyrrole compound disclosed herein, after step b), can further comprise a step of separating at least a portion or isolating at least a portion (and in some cases, all) of the pyrrole compound from the reaction product mixture. This can be accomplished using any suitable technique, such as extraction, filtration, drying, evaporation, distillation, and the like, or any combination thereof.

Unexpectedly, the disclosed two-step synthesis efficiently converts the furan compound to the γ-dicarbonyl compound, and then produces the pyrrole compound in a surprisingly high yield. For instance, a molar yield to the pyrrole compound can be at least 60 mol %, and more often, at least 70 mol %, at least 80 mol %, at least 90 mol %, at least 95 mol %, or at least 97 mol %. The molar yield is based on the initial moles of the furan compound. Unless otherwise indicated, the compositional aspects of pyrrole products (or reaction product mixtures containing pyrrole products) are disclosed in mol %. Any disclosure herein of a compositional aspect in mol % is also meant to encompass the same compositional aspect in area % (area percentage determined using a gas chromatograph, as described herein), because the disclosed processes and resultant products are often analyzed or evaluated in this manner, although the values using area % and mol % are not identical. As a representative example, a disclosure that the pyrrole compound can be produced in a yield of at least 90 mol % is meant also to alternatively disclose that the pyrrole compound can be produced in a yield of at least 90 area %.

Solid Acid Catalysts

In step a) of the processes disclosed herein for producing a pyrrole compound, the furan compound, a solid acid catalyst, and water are contacted to form a reaction mixture comprising a γ-dicarbonyl compound. Any suitable solid acid catalyst can be used. Illustrative and representative examples of suitable solid acid catalysts can include solid acid catalyst resins. Solid acid catalyst resins can include a styrene-divinylbenzene resin, a functionalized styrene-divinylbenzene resin, a 4-vinylpyridine divinylbenzene resin, a functionalized 4-vinylpyridine divinylbenzene resin, an ionomer resin, a tetrafluoroethylene polymer resin modified with perfluorovinyl ether groups terminated with sulfonate groups, or any combination thereof, alternatively, a styrene-divinylbenzene resin, a 4-vinylpyridine divinylbenzene resin, an ionomer resin, a tetrafluoroethylene resin modified with perfluorovinyl ether groups terminated with sulfonate groups, and the like, as well as combinations thereof. Some of these solid acid catalyst types are available under the Amberlyst® resin and Nafion® resin tradenames.

In one aspect of this invention, step a) comprises contacting the furan compound, the solid acid catalyst, and water to form the reaction mixture comprising the γ-dicarbonyl compound, and the solid acid catalyst comprises a styrene-divinylbenzene resin. In another aspect, step a) comprises contacting the furan compound, the solid acid catalyst, and water to form the reaction mixture comprising the γ-dicarbonyl compound, and the solid acid catalyst comprises a 4-vinylpyridine divinylbenzene resin. In yet another aspect, step a) comprises contacting the furan compound, the solid acid catalyst, and water to form the reaction mixture comprising the γ-dicarbonyl compound, and the solid acid catalyst comprises a tetrafluoroethylene resin modified with perfluorovinyl ether groups terminated with sulfonate groups.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Gas Chromatograph (GC) analyses were conducted on an Agilent 7890 GC System, using a HP-Innowax column (polyethyleneglycol, capillary 30 m×0.25 mm×25 μm nominal), with 40° C. temperature hold for 2 minutes followed by ramping at a rate of 8° C./min from 40° C. to 220° C., then 15° C./min to 270° C., which is held for 15 minutes. GC analysis column eluents were determined using a flame ionization detector. Standards for 2,5-dimethylfuran (~3 min retention time in FIGS. 1-3) and 2,5-hexanedione (~12.2-12.6 min retention time, depending upon the size of the peak in FIGS. 1-3) were used to identify the reactants and products, and to monitor the course of the reactions.

Examples 1-5

Synthesis of a γ-Dicarbonyl Compound (2,5-hexanedione) from a Furan Compound (2,5-dimethytfiran, DMF)

All liquid raw materials were pressured into an autoclave. If solids were used, these were added before closing the autoclave. The autoclave was then pressured to 50 psig using nitrogen and the pressure was released three times to remove air from system. Approximately 50-75 psig of nitrogen was added to the autoclave and then heated to the desired temperature. At reaction conditions, the pressure was in the 90-140 psig range. The reaction was monitored by GC until conversion stopped. Some initial samples were biphasic. When the sample was biphasic, 2-propanol was added to the sample to homogenize the sample for GC analysis.

Figure 1:
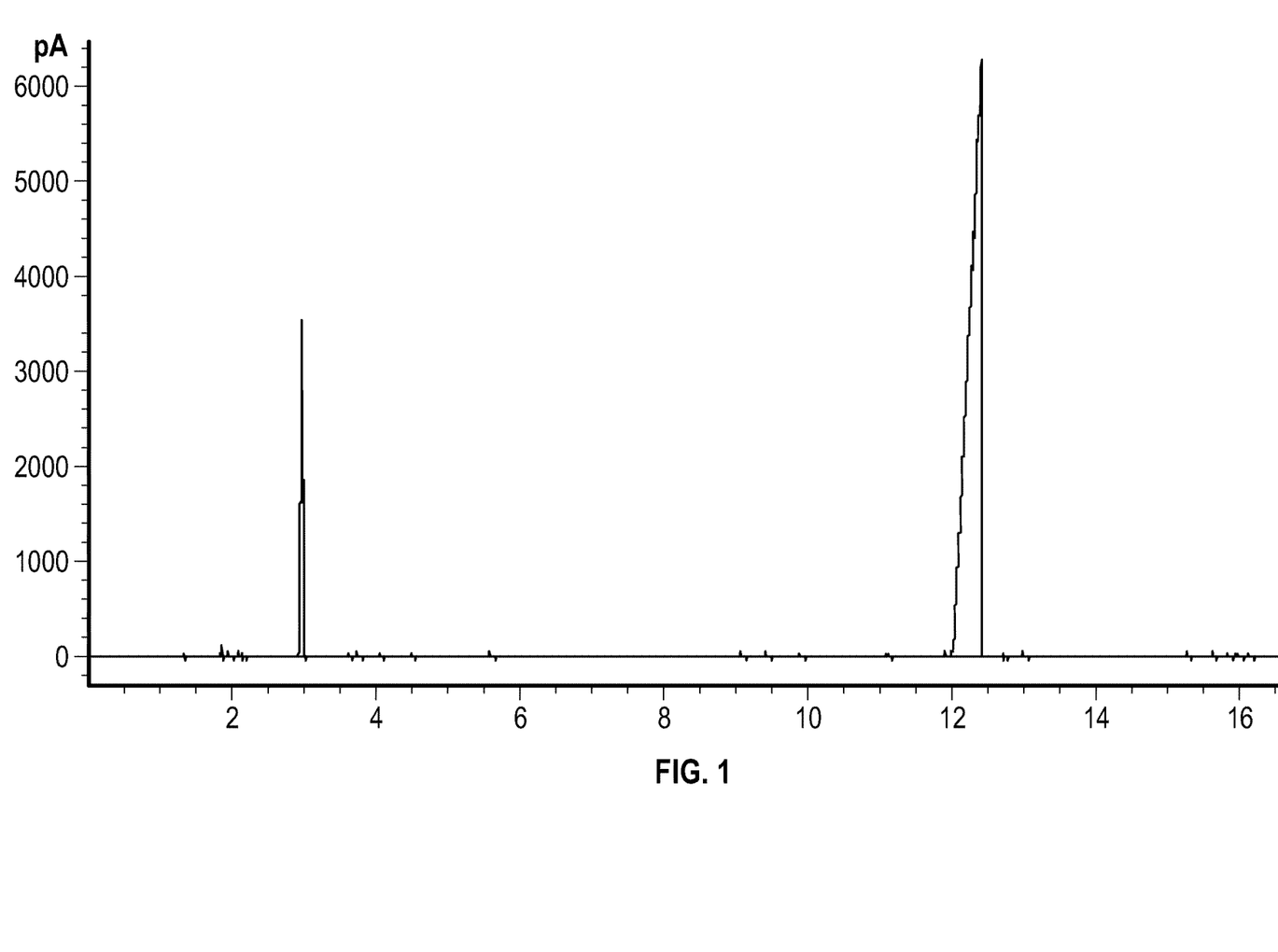
FIG. 1 presents a gas chromatograph plot of the reaction mixture of Example 1 containing 2,5-hexanedione.

In Example 1, DMF was mixed with water and concentrated sulfuric acid, as summarized in Table I. The reaction was conducted at 100° C. for 3 hr followed by 140° C. for 1 hr. FIG. 1 is a GC plot of the reaction mixture of Example 1. Conversion of DMF was 93 area % (~93 mol %, values in molar percentages are comparable to the area percentages). While the conversion using sulfuric acid was acceptable, the presence of the sulfuric acid presents a difficult separations process prior to use of the reaction mixture containing 2,5-hexanedione in a reaction with a base (e.g., ammonia or an ammonium salt) to form the subsequent pyrrole compound.

Figure 2:
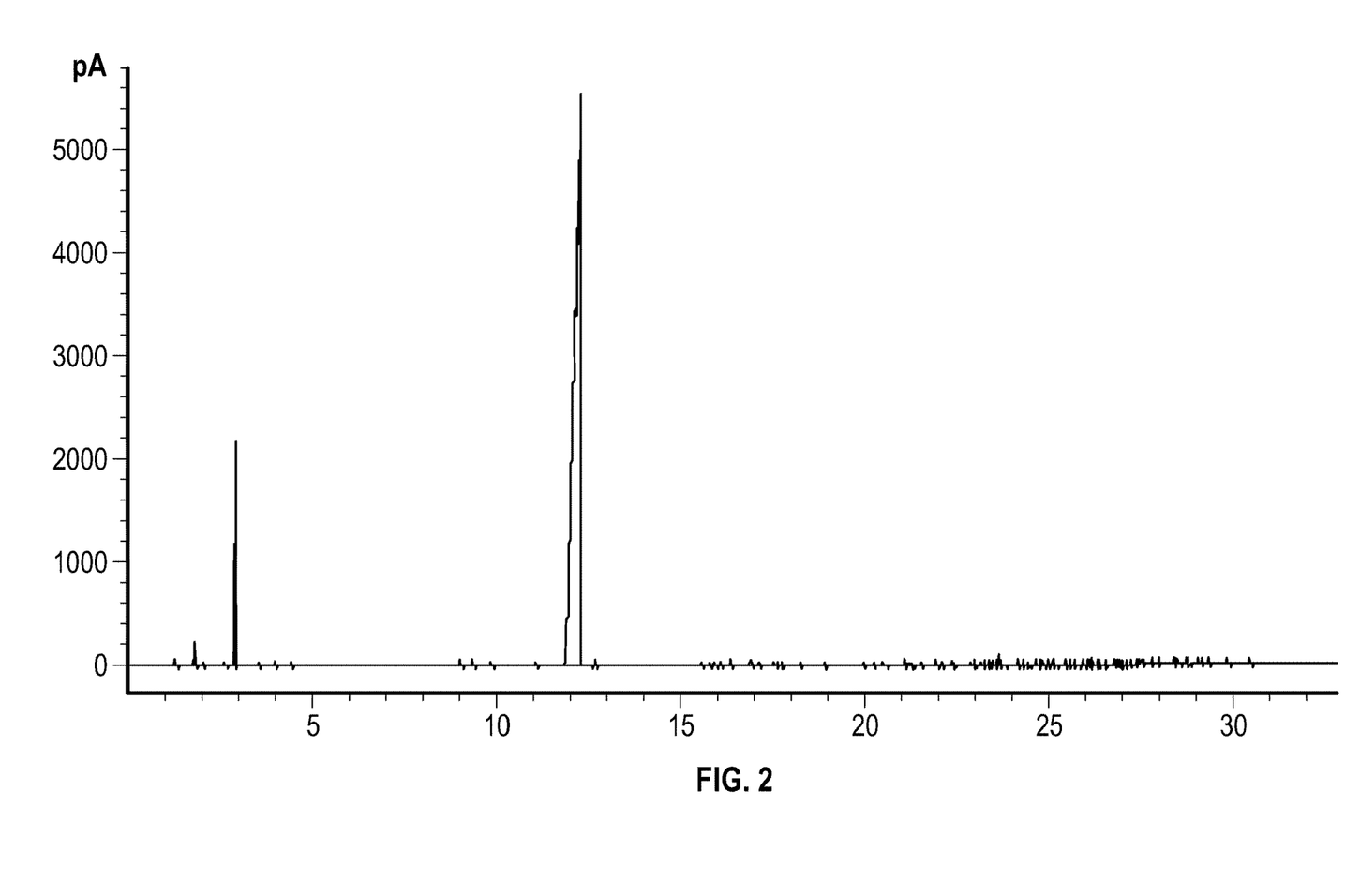
FIG. 2 presents a gas chromatograph plot of the reaction mixture of Example 2 containing 2,5-hexanedione.

In Example 2, DMF was mixed with water and methanesulfonic acid (>99%), as summarized in Table II. The reaction was conducted at 140° C. for 3 hr. FIG. 2 is a GC plot of the reaction mixture of Example 2. Conversion of DMF was 95.7 area % (~95.7 mol %). Note the large number of components on the GC curve in the 15-25 min range. Similar to Example 1, the presence of residual methanesulfonic acid presents a difficult separations process prior to use of the reaction mixture containing 2,5-hexanedione in a reaction with a base (e.g., ammonia or an ammonium salt) to form the subsequent pyrrole compound.

Figure 3:
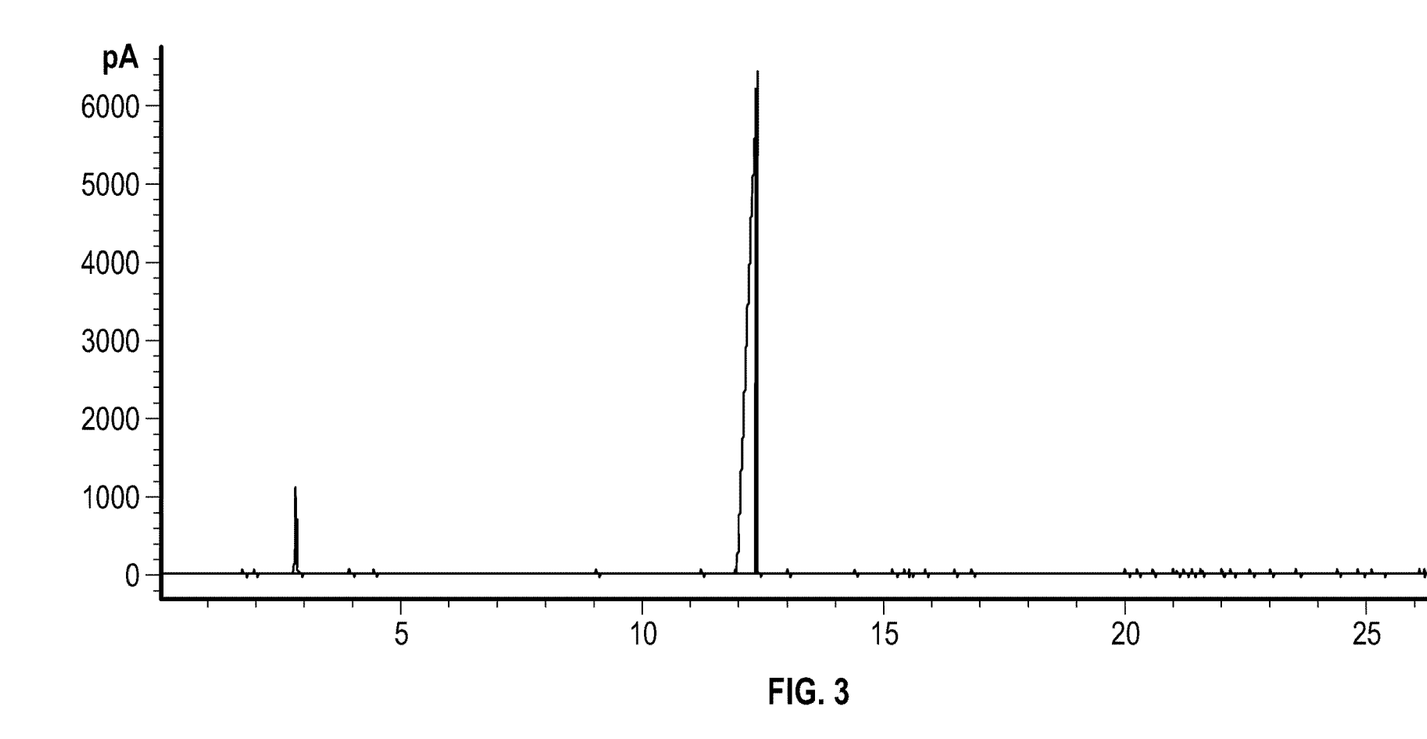
FIG. 3 presents a gas chromatograph plot of the reaction mixture of Example 3 containing 2,5-hexanedione.

In Example 3, DMF was mixed with water and Amberlyst 36 (a styrene divinylbenzene solid acid catalyst resin), as summarized in Table III. After the final nitrogen purge cycle, 75 psig of nitrogen was added and the reactor contents were heated to 145° C. The reaction was sampled hourly to monitor progress and was deemed complete after 4 hr. Pressures were in the 125-140 psig range. FIG. 3 is a GC plot of the reaction mixture of Example 3. Unexpectedly, the reaction mixture contained approximately 3 area % (mol %) 2,5-dimethylfuran and 97 area % (mol %) 2,5-hexanedione. DMF conversion was 97 area % (mol %).

In Example 4, the reaction mixture of Example 3 was further processed to isolate the 2,5-hexanedione. The reactor was drained, and a rotary evaporator was used to strip any remaining water from the crude reaction mixture. The conditions used to strip the water were a 70° C. water bath and the pressure was reduced to below 100 torr. After this step, 267.5 g of crude product remained in the kettle.

This crude product was then vacuum distilled to yield a pure overhead product. The flask was heated to 80° C. at 400 torr to remove any remaining light components. The temperature was eventually increased to 120° C. and the pressure decreased to 50 torr to yield highly pure overhead 2,5-hexanedione product (~98 area % purity by GC). A 5:5 reflux ratio was used throughout. This distillation took approximately 25 hr over multiple days to complete.

Approximately 221 g of the highly pure overhead product were collected (72 area % yield). However, the final kettle (42.5 g) was also 98 area % pure by GC, but had a slightly darker color, and couldn't be distilled any further due to the level in flask. Had this material also been recovered, the overall yield of the 2,5-hexanedione would be 86 area % (~86 mol %). Beneficially, it was found that the 2,5-hexanedione was easy to separate in very purity from the reaction mixture of Example 3.

In Example 5, DMF was mixed with water and Amberlyst 15 (solid acid catalyst; styrene divinylbenzene), as summarized in Table IV. After the final nitrogen purge cycle, 50 psig of nitrogen was added and the reactor contents were heated to 110° C. The reaction was sampled hourly to monitor progress and was deemed complete after 20 hr. DMF conversion was 97 area % (mol %), similar to Example 3.

In addition to higher conversions of DMF using the solid acid catalysts, as compared to sulfuric acid and methanesulfonic acid (Examples 1-2), there are additional advantages to the use the solid acid catalysts. For sulfuric acid and methanesulfonic acid, a further removal step likely would be required, either extraction using a base or forming a salt with ammonia. An additional solvent would be needed for the extraction. Further, if the acid is present during water removal, such as during a step to isolate the 2,5-hexanedione, the reverse reaction can occur and DMF can be reformed. In contrast, these issues are not relevant when a solid acid catalyst is used, since the solid catalyst can be simply filtered out prior to water removal.

Constructive Example 6

Constructive Synthesis of a Pyrrole Compound (2,5-dimethylpyrrole) from a γ-dicarbonyl Compound (2,5-hexanedione)

The 2,5-hexanedione (142 g, ~90% purity) can be charged into a 250-mL round bottom flask equipped with a stirbar, heating mantle, reflux condenser, and nitrogen inlet and outlet. The reaction flask is heated to 60° C. and ammonium carbonate (150 g) is charged over a period of 90 min. Gas evolution will be apparent during this heating stage. Once gas evolution stops, the temperature is increased to 80° C. for 30 min. After cooling to room temperature, the two-phase reaction mixture is separated in a separatory funnel. The aqueous phase produced during the reaction is separated from the organic phase and the organic phase is washed with an additional 125 mL of water. A total of 90 g of 2,5-dimethylpyrrole (85% molar yield, based on the dione) is collected at a purity, as determined by GC analysis, of 96 area % (approximately 96 mol %).

TABLE I

Summary of Example 1.

| Material | Amount (g) | Amount (mol) |
|---|---|---|
| 2,5-dimethylfuran | 100 | 1.04 |
| Water | 37.4 | 2.08 |
| Sulfuric Acid | 2.0 | — |

TABLE II

Summary of Example 2.

| Material | Amount (g) | Amount (mol) |
|---|---|---|
| 2,5-dimethylfuran | 100 | 1.04 |
| Water | 37.4 | 2.08 |
| Methanesulfonic Acid | 2.0 | — |

TABLE III

Summary of Example 3.

| Material | Amount (g) | Amount (mol) |
|---|---|---|
| 2,5-dimethylfuran | 250 | 2.60 |
| Water | 140 | 7.78 |
| Amberlyst 36 | 15 | — |

TABLE IV

Summary of Example 5.

| Material | Amount (g) | Amount (mol) |
|---|---|---|
| 2,5-dimethylfuran | 250 | 2.60 |
| Water | 94 | 5.22 |
| Amberlyst 15 | 7.5 | — |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for producing a pyrrole compound, the process comprising:

a) contacting a furan compound, a solid acid catalyst, and water to form a reaction mixture comprising a γ-dicarbonyl compound; and b) contacting the γ-dicarbonyl compound with ammonia, an ammonium salt, or a combination thereof, to form a reaction product mixture comprising the pyrrole compound.

Aspect 2. The process defined in aspect 1, wherein the furan compound (F1), the γ-dicarbonyl compound (D1), and the pyrrole compound (P1) have the following formulas:

(F1)

(D1)

(P1)

wherein R, $R^1$, $R^2$, and $R^3$ independently are a hydrogen atom, a $C_1$-$C_{30}$ organyl group, or a $C_3$-$C_{60}$ silyl group.

Aspect 3. The process defined in aspect 2, wherein at least one of R, $R^1$, $R^2$, and $R^3$ is not a hydrogen atom.

Aspect 4. The process defined in aspect 2 or 3, wherein R, $R^1$, $R^2$, and $R^3$ independently are a hydrogen atom or a $C_1$-$C_{18}$ hydrocarbyl group.

Aspect 5. The process defined in aspect 2 or 3, wherein R and $R^1$ independently are a $C_1$-$C_{18}$ hydrocarbyl group, and $R^2$ and $R^3$ are a hydrogen atom.

Aspect 6. The process defined in any one of aspects 2-5, wherein R and $R^1$ independently are a methyl group, an ethyl group, an n-propyl group, an iso-propyl group, an n-butyl group, a t-butyl group, a phenyl group, a benzyl group, a tolyl group, or a xylyl group.

Aspect 7. The process defined in any one of aspects 2-6, wherein R and $R^1$ are a methyl group, and $R^2$ and $R^3$ are hydrogen.

Aspect 8. The process defined in aspect 1, wherein the pyrrole compound comprises 2,5-dimethylpyrrole, 2-methyl-5-ethylpyrrole, 2,5-diethylpyrrrole, 2-ethyl-5-methylpyrrole, 2-ethyl-5-n-propylpyrrole, 2,5-di-n-propylpyrrole, 2,5-diisopropylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,3,5-triethylpyrrrole, 2,3,5-tri-n-butylpyrrole, 2,3,5-tri-n-pentylpyrrole, 2,3,5-tri-n-hexylpyrrole, 2,3,5-tri-n-heptylpyrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-dibenzylpyrrole, 2,4-dimethylpyrrole, 2-methyl-4-isopropylpyrrole, 2,4-dimethyl-3-ethylpyrrole, 2,4-diethylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-dimethylpyrrole, 3,4-diethylpyrrole, 3,4-diisopropylpyrrole, 3,4-di-sec-butylpyrrole, 3,4-diisobutylpyrrole, 3,4-di-t-butylpyrrole, 3,4-di-neopentylpyrrole, or any combination thereof.

Aspect 9. The process defined in aspect 1, wherein the pyrrole compound comprises 2,5-dimethylpyrrole.

Aspect 10. The process defined in any one of aspects 1-9, wherein the solid acid catalyst comprises a styrene-divinylbenzene resin, a 4-vinylpyridine divinylbenzene resin, an ionomer resin, a tetrafluoroethylene resin modified with perfluorovinyl ether groups terminated with sulfonate groups, or any combination thereof.

Aspect 11. The process defined in any one of aspects 1-9, wherein the solid acid catalyst comprises a styrene-divinylbenzene resin.

Aspect 12. The process defined in any one of aspects 1-9, wherein the solid acid catalyst comprises a 4-vinylpyridine divinylbenzene resin.

Aspect 13. The process defined in any one of aspects 1-9, wherein the solid acid catalyst comprises a tetrafluoroethylene resin modified with perfluorovinyl ether groups terminated with sulfonate groups.

Aspect 14. The process defined in any one of aspects 1-13, wherein step b) comprises contacting the γ-dicarbonyl compound with ammonia.

Aspect 15. The process defined in any one of aspects 1-13, wherein step b) comprises contacting the γ-dicarbonyl compound with the ammonium salt (e.g., ammonium hydroxide, ammonium acetate, ammonium carbonate, ammonium bicarbonate, ammonium chloride, ammonium nitrate, ammonium phosphate, ammonium sulfate, or any combination thereof).

Aspect 16. The process defined in any one of aspects 1-15, wherein step a) is conducted at any molar ratio of water to the furan compound described herein (e.g., in a range from 0.5:1 to 10:1, from 1:1 to 7.5:1, or from 1.5:1 to 5:1, among other disclosed water to the furan compound molar ratios).

Aspect 17. The process defined in any one of aspects 1-16, wherein step a) is conducted at any temperature below the maximum operating temperature of the solid acid catalyst.

Aspect 18. The process defined in any one of aspects 1-17, wherein step a) is conducted at any temperature disclosed herein (e.g., in a range from 80° C. to 180° C., from 100° C. to 155° C., or from 120° C. to 150° C., among other disclosed temperatures).

Aspect 19. The process defined in any one of aspects 1-18, wherein step a) is conducted at any pressure sufficient to maintain water in the liquid phase.

Aspect 20. The process defined in any one of aspects 1-19, wherein step a) is conducted at any pressure disclosed herein (e.g., in a range from 25 to 150 psig, or from 50 to 125 psig, among other disclosed pressures).

Aspect 21. The process defined in any one of aspects 1-20, wherein step a) is conducted in a stirred tank reactor or a fixed bed reactor.

Aspect 22. The process defined in any one of aspects 1-21, wherein step a) is conducted in a stirred tank reactor for any time period disclosed herein (e.g., from 10 min to 8 hr, or from 1 hr to 5 hr, among other disclosed time periods).

Aspect 23. The process defined in aspect 21 or 22, wherein step a) is conducted in a stirred tank reactor at any weight ratio of the furan compound to the solid acid catalyst disclosed herein (e.g., in a range from 5:1 to 50:1, from 7.5:1 to 40:1, or from 10:1 to 25:1, among other disclosed furan compound to the solid acid catalyst weight ratios).

Aspect 24. The process defined in any one of aspects 21-23, wherein step a) is conducted in a stirred tank reactor, and a conversion of the furan compound (or a yield to the γ-dicarbonyl compound) is any molar conversion (or molar yield) disclosed herein (e.g., at least 70%, at least 80%, at least 90%, at least 95%, or at least 97%).

Aspect 25. The process defined in aspect 21, wherein step a) is conducted in a fixed bed reactor at any furan compound WHSV disclosed herein (e.g., in a range from 0.01 to 5, from 0.05 to 4, from 0.1 to 3, from 0.15 to 2, or from 0.2 to 1 among other disclosed furan compound WHSVs).

Aspect 26. The process defined in aspect 21 or 25, wherein step a) is conducted in a fixed bed reactor, and a single pass conversion of the furan compound (or a single pass yield to the γ-dicarbonyl compound) is any single pass molar conversion (or single pass molar yield) disclosed herein (e.g., at least 10%, at least 25%, at least 50%, at least 75%, or at least 90%).

Aspect 27. The process defined in any one of aspects 1-26, further comprising a step of separating at least a portion (and in some cases, all) of the γ-dicarbonyl compound from the reaction mixture using any suitable technique or any technique disclosed herein, e.g., extraction, filtration, evaporation, distillation, etc., or any combination thereof, prior to step b).

Aspect 28. The process defined in any one of aspects 1-27, further comprising a step of separating at least a portion (and in some cases, all) of the solid acid catalyst from the reaction mixture using any suitable technique or any technique disclosed herein, e.g., extraction, filtration, evaporation, distillation, or any combination thereof, prior to step b).

Aspect 29. The process defined in any one of aspects 1-28, wherein step b) is conducted at any temperature disclosed herein (e.g., in a range from 70° C. to 150° C., or from 80° C. to 130° C., among other disclosed temperatures).

Aspect 30. The process defined in any one of aspects 1-29, wherein step b) is conducted for any time period disclosed herein (e.g., from 30 min to 8 hr, or from 2 hr to 5 hr, among other disclosed time periods).

Aspect 31. The process defined in any one of aspects 1-30, wherein the reaction product mixture comprises an organic phase and an aqueous phase.

Aspect 32. The process defined in any one of aspects 1-31, further comprising a step of separating at least a portion (and in some cases, all) of the water from the reaction product mixture (e.g., phase cut) after step b).

Aspect 33. The process defined in any one of aspects 1-32, further comprising a step of separating at least a portion (and in some cases, all) of the pyrrole compound from the reaction product mixture using any suitable technique or any technique disclosed herein, e.g., extraction, filtration, drying, evaporation, distillation, etc., or any combination thereof, after step b).

Aspect 34. The process defined in any one of aspects 1-33, wherein the pyrrole compound is produced in any molar yield disclosed herein (e.g., at least 60%, at least 70%, at least 80%, at least 90%, at least 95%, or at least 97%, based on the furan compound).

I claim:

1. A process for producing a pyrrole compound, the process comprising:
   a) contacting a furan compound, a solid acid catalyst, and water to form a reaction mixture comprising a γ-dicarbonyl compound, wherein a molar ratio of water to the furan compound is in a range from 0.5:1 to 10:1; and
   b) contacting the γ-dicarbonyl compound with ammonia, an ammonium salt, or a combination thereof, to form a reaction product mixture comprising the pyrrole compound.

2. The process of claim 1, wherein the furan compound (F1), the γ-dicarbonyl compound (D1), and the pyrrole compound (P1) have the following formulas:

wherein R, $R^1$, $R^2$, and $R^3$ independently are a hydrogen atom, a $C_1$-$C_{30}$ organyl group, or a $C_3$-$C_{60}$ silyl group.

3. The process of claim 2, wherein R, $R^1$, $R^2$, and $R^3$ independently are a hydrogen atom or a $C_1$-$C_{18}$ hydrocarbyl group.

4. The process of claim 2, wherein R and $R^1$ independently are a $C_1$-$C_{18}$ hydrocarbyl group, and $R^2$ and $R^3$ are a hydrogen atom.

5. The process of claim 2, wherein R and $R^1$ independently are a methyl group, an ethyl group, an n-propyl group, an iso-propyl group, an n-butyl group, a t-butyl group, a phenyl group, a benzyl group, a tolyl group, or a xylyl group.

6. The process of claim 1, wherein the pyrrole compound comprises 2,5-dimethylpyrrole.

7. The process of claim 1, wherein the solid acid catalyst comprises a styrene-divinylbenzene resin, a 4-vinylpyridine divinylbenzene resin, an ionomer resin, a tetrafluoroethylene resin modified with perfluorovinyl ether groups terminated with sulfonate groups, or any combination thereof.

8. The process of claim 1, wherein the solid acid catalyst comprises a styrene-divinylbenzene resin.

9. The process of claim 1, wherein step a) is conducted at:
a temperature below the maximum operating temperature of the solid acid catalyst; and
a pressure sufficient to maintain water in the liquid phase.

10. The process of claim 1, wherein step a) is conducted at:
a temperature in a range from 80° C. to 180° C.; and
a pressure in a range from 25 to 150 psig.

11. The process of claim 1, wherein the molar ratio of water to the furan compound is in a range from 1:1 to 7.5:1.

12. The process of claim 1, wherein step a) is conducted in a stirred tank reactor at a weight ratio of the furan compound to the solid acid catalyst in a range from 5:1 to 50:1.

13. The process of claim 1, wherein a conversion of the furan compound is at least 90 mol %.

14. The process of claim 13, wherein a yield to the γ-dicarbonyl compound is at least 80 mol %.

15. The process of claim 1, wherein step a) is conducted in a fixed bed reactor at a furan compound WHSV in a range from 0.01 to 5.

16. The process of claim 1, further comprising:
a step of separating at least a portion of the y-dicarbonyl compound from the reaction mixture prior to step b); and/or
a step of separating at least a portion of the solid acid catalyst from the reaction mixture prior to step b).

17. The process of claim 1, wherein step b) comprises contacting the γ-dicarbonyl compound with the ammonium salt, and wherein the ammonium salt comprises ammonium hydroxide, ammonium acetate, ammonium carbonate, ammonium bicarbonate, ammonium chloride, ammonium nitrate, ammonium phosphate, ammonium sulfate, or any combination thereof.

18. The process of claim 1, wherein:
the reaction product mixture comprises an organic phase and an aqueous phase; and
the process further comprises a step of separating at least a portion of the water from the reaction product mixture after step b).

19. The process of claim 1, wherein the pyrrole compound is produced in a yield of at least 70 mol %, based on the furan compound.

20. The process of claim 1, further comprising a step of separating at least a portion of the pyrrole compound from the reaction product mixture after step b).

21. The process of claim 1, wherein step a) is conducted at a temperature in a range from 110° C. to 170° C.

* * * * *